United States Patent
Christian

(12) 
(10) Patent No.: US 12,274,490 B2
(45) Date of Patent: *Apr. 15, 2025

(54) IRRIGATED ABLATION ELECTRODE ASSEMBLIES

(71) Applicant: St. Jude Medical, Atrial Fibrillation Division, Inc., St. Paul, MN (US)

(72) Inventor: Steven C. Christian, New Brighton, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 275 days.

This patent is subject to a terminal disclaimer.

(21) Appl. No.: 17/216,309

(22) Filed: Mar. 29, 2021

(65) Prior Publication Data
US 2021/0282846 A1  Sep. 16, 2021

Related U.S. Application Data

(60) Continuation of application No. 15/873,574, filed on Jan. 17, 2018, now Pat. No. 10,987,162, which is a
(Continued)

(51) Int. Cl.
*A61B 18/14* (2006.01)
*A61B 18/00* (2006.01)
*A61B 18/02* (2006.01)

(52) U.S. Cl.
CPC ........ *A61B 18/1492* (2013.01); *A61B 2018/00029* (2013.01); *A61B 2018/00083* (2013.01);
(Continued)

(58) Field of Classification Search
CPC ............... A61B 18/02; A61B 18/1492; A61B 2018/00029; A61B 2018/00083;
(Continued)

(56) References Cited

U.S. PATENT DOCUMENTS

| 5,290,263 A | 3/1994 | Wigness et al. |
| 5,348,554 A | 9/1994 | Imran et al. |

(Continued)

FOREIGN PATENT DOCUMENTS

| EP | 2204132 A1 | 7/2010 |
| JP | S61-168344 | 7/1986 |

(Continued)

OTHER PUBLICATIONS

International Search Report and Written Opinion of ISA for PCT/US2012/023355 mailed Jun. 4, 2012.
(Continued)

*Primary Examiner* — Michael F Peffley
(74) *Attorney, Agent, or Firm* — Armstrong Teasdale LLP

(57) ABSTRACT

An irrigated ablation electrode assembly comprises a distal member, a first manifold, and a second manifold. The distal member includes an outer surface; an inner surface; and at least one radially extending passageway that extends from the inner surface of the distal member to the outer surface of the distal member. The first manifold includes an outer surface, an inner cavity, and at least one radially extending passageway that extends from the inner cavity to the outer surface of the first manifold. The second manifold includes an outer surface, an inner surface, and at least one radially extending passageway that extends from the inner surface of the second manifold to the outer surface of the second manifold. Other irrigated ablation electrode assemblies are also presented.

20 Claims, 8 Drawing Sheets

Related U.S. Application Data continuation of application No. 14/326,823, filed on Jul. 9, 2014, now Pat. No. 9,901,397, which is a division of application No. 12/971,645, filed on Dec. 17, 2010, now Pat. No. 8,814,857.

(52) U.S. Cl.
CPC ............. *A61B 2018/00714* (2013.01); *A61B 2018/00791* (2013.01); *A61B 2018/00815* (2013.01); *A61B 2018/00821* (2013.01); *A61B 2018/00863* (2013.01); *A61B 2018/00875* (2013.01); *A61B 18/02* (2013.01); *A61B 2217/007* (2013.01); *A61B 2218/002* (2013.01)

(58) Field of Classification Search
CPC ........... A61B 2018/00714; A61B 2018/00791; A61B 2018/00815; A61B 2018/00821; A61B 2018/00863; A61B 2018/00875; A61B 2217/007; A61B 2218/002
See application file for complete search history.

(56) References Cited

U.S. PATENT DOCUMENTS

| | | | |
|---|---|---|---|
| 5,472,441 A | 12/1995 | Edwards et al. | |
| 5,545,161 A * | 8/1996 | Imran | A61B 18/1492 606/41 |
| 5,688,267 A | 11/1997 | Panescu et al. | |
| 5,735,846 A | 4/1998 | Panescu et al. | |
| 5,792,140 A | 8/1998 | Tu et al. | |
| 5,868,741 A * | 2/1999 | Chia | A61B 18/1492 606/41 |
| 5,897,552 A | 4/1999 | Edwards et al. | |
| 5,902,328 A | 5/1999 | Lafontaine et al. | |
| 6,010,500 A | 1/2000 | Sherman et al. | |
| 6,017,338 A | 1/2000 | Brucker et al. | |
| 6,050,993 A | 4/2000 | Tu et al. | |
| 6,068,653 A | 5/2000 | Lafontaine | |
| 6,171,275 B1 | 1/2001 | Webster, Jr. | |
| 6,217,576 B1 | 4/2001 | Tu et al. | |
| 6,233,476 B1 | 5/2001 | Strommer et al. | |
| 6,328,735 B1 | 12/2001 | Curley et al. | |
| 6,464,700 B1 | 10/2002 | Koblish et al. | |
| 6,498,944 B1 | 12/2002 | Ben-Haim et al. | |
| 6,506,189 B1 | 1/2003 | Rittman et al. | |
| 6,514,251 B1 | 2/2003 | Ni et al. | |
| 6,522,930 B1 | 2/2003 | Schaer et al. | |
| 6,575,969 B1 | 6/2003 | Rittman et al. | |
| 6,579,288 B1 | 6/2003 | Swanson et al. | |
| 6,616,655 B1 | 9/2003 | Falwell et al. | |
| 6,690,963 B2 | 2/2004 | Ben-Haim et al. | |
| 6,788,967 B2 | 9/2004 | Ben-Haim et al. | |
| 6,936,047 B2 | 8/2005 | Nasab et al. | |
| 7,197,354 B2 | 3/2007 | Sobe | |
| 7,263,397 B2 | 8/2007 | Hauck et al. | |
| RE39,863 E | 10/2007 | Smith | |
| 7,344,533 B2 | 3/2008 | Pearson et al. | |
| 7,386,339 B2 | 6/2008 | Strommer et al. | |
| 7,389,148 B1 | 6/2008 | Morgan | |
| 7,536,218 B2 | 5/2009 | Govari et al. | |
| 7,591,816 B2 | 9/2009 | Wang et al. | |
| 7,776,034 B2 | 8/2010 | Kampa | |
| 7,815,635 B2 * | 10/2010 | Wittkampf | A61B 18/1492 606/49 |
| 7,824,406 B2 | 11/2010 | Wang et al. | |
| 7,826,905 B2 | 11/2010 | Chitre et al. | |
| 7,998,141 B2 | 8/2011 | Wittkampf et al. | |
| 8,273,082 B2 | 9/2012 | Wang et al. | |
| 9,084,610 B2 | 7/2015 | Goshgarian et al. | |
| 2002/0123749 A1 | 9/2002 | Jain | |
| 2002/0169445 A1 | 11/2002 | Jain et al. | |
| 2003/0004506 A1 | 1/2003 | Messing | |
| 2003/0060822 A1 | 3/2003 | Schaer et al. | |
| 2003/0195510 A1 | 10/2003 | Schaer | |
| 2004/0210283 A1 | 10/2004 | Rose et al. | |
| 2004/0215183 A1 | 10/2004 | Hoey et al. | |
| 2005/0055019 A1 | 3/2005 | Skarda | |
| 2005/0070894 A1 | 3/2005 | McClurken | |
| 2005/0090816 A1 | 4/2005 | Mclurken et al. | |
| 2005/0177209 A1 | 8/2005 | Leung et al. | |
| 2006/0122593 A1 | 6/2006 | Jun | |
| 2006/0287650 A1 | 12/2006 | Cao et al. | |
| 2007/0043349 A1 | 2/2007 | Swanson et al. | |
| 2007/0049915 A1 | 3/2007 | Haemmerich et al. | |
| 2007/0270791 A1 | 11/2007 | Wang et al. | |
| 2008/0065062 A1 | 3/2008 | Leung et al. | |
| 2008/0071267 A1 | 3/2008 | Wang et al. | |
| 2008/0091193 A1 | 4/2008 | Kauphusman et al. | |
| 2008/0147060 A1 | 6/2008 | Choi | |
| 2008/0161795 A1 | 7/2008 | Wang et al. | |
| 2008/0161797 A1 | 7/2008 | Wang et al. | |
| 2008/0167646 A1 | 7/2008 | Godara et al. | |
| 2008/0294158 A1 | 11/2008 | Pappone et al. | |
| 2009/0093811 A1 | 4/2009 | Koblish et al. | |
| 2009/0125016 A1 * | 5/2009 | Wang | A61B 18/1492 606/41 |
| 2009/0125017 A1 | 5/2009 | Wang et al. | |
| 2009/0163911 A1 | 6/2009 | Cao et al. | |
| 2009/0163913 A1 | 6/2009 | Wang et al. | |
| 2009/0171187 A1 | 7/2009 | Gerhart et al. | |
| 2009/0171188 A1 | 7/2009 | Paul et al. | |
| 2009/0177193 A1 | 7/2009 | Wang et al. | |
| 2009/0240248 A1 | 9/2009 | Deford et al. | |
| 2009/0240249 A1 | 9/2009 | Chan et al. | |
| 2009/0312756 A1 | 12/2009 | Schlesinger et al. | |
| 2010/0005707 A1 | 3/2010 | Roman et al. | |
| 2010/0057072 A1 | 3/2010 | Roman et al. | |
| 2010/0069921 A1 | 3/2010 | Miller et al. | |
| 2010/0137859 A1 | 6/2010 | Wang | |
| 2010/0152724 A1 | 6/2010 | Marion et al. | |
| 2010/0152727 A1 | 6/2010 | Gibson | |
| 2010/0152731 A1 | 6/2010 | De La Rama et al. | |
| 2010/0168729 A1 * | 7/2010 | Wang | A61M 25/007 606/41 |
| 2010/0168736 A1 | 7/2010 | Wang | |
| 2010/0174177 A1 | 7/2010 | Wu | |
| 2010/0211070 A1 | 8/2010 | Subramaniam et al. | |
| 2010/0286684 A1 | 11/2010 | Hata et al. | |
| 2011/0092969 A1 | 4/2011 | Wang et al. | |
| 2011/0118724 A1 | 5/2011 | Turner et al. | |
| 2011/0264089 A1 | 10/2011 | Zirkle et al. | |
| 2011/0282342 A1 | 11/2011 | Giovanni et al. | |
| 2012/0035605 A1 | 2/2012 | Tegg et al. | |
| 2012/0165809 A1 | 6/2012 | Christian et al. | |

FOREIGN PATENT DOCUMENTS

| | | |
|---|---|---|
| JP | H06-254103 | 9/1994 |
| JP | 2007-509693 | 4/2007 |
| JP | 2009-537243 | 10/2009 |
| JP | 2010-505596 | 2/2010 |
| JP | 2012-531967 | 12/2012 |
| WO | 9634569 | 11/1996 |
| WO | 03024349 A1 | 3/2003 |
| WO | 2005048858 | 6/2005 |
| WO | 2007136979 | 11/2007 |
| WO | 2008045925 | 4/2008 |
| WO | 2008082988 | 10/2008 |
| WO | 2008083000 | 10/2008 |
| WO | 2008083003 | 10/2008 |
| WO | 2009082574 | 2/2009 |
| WO | 2009070446 | 6/2009 |
| WO | 20110084-44 | 1/2011 |
| WO | 2012091793 A1 | 7/2012 |

OTHER PUBLICATIONS

International Search Report and Written Opinion of ISA for PCT/US2012/026759 mailed Jul. 5, 2012.

(56) References Cited

OTHER PUBLICATIONS

International Search Report and Written Opinion of ISA for PCT/US2011/059111 mailed Apr. 13, 2012.

* cited by examiner

IRRIGATED ABLATION ELECTRODE ASSEMBLIES

CROSS-REFERENCE TO RELATED APPLICATIONS

This application is a continuation of U.S. patent application Ser. No. 15/873,574, filed 17 Jan. 2018 (the '574 application), now U.S. Pat. No. 10,987,162, issued 27 Apr. 2021, which is a continuation of U.S. patent application Ser. No. 14/326,823, filed 9 Jul. 2014 (the '823 application), now U.S. Pat. No. 9,901,397, issued 27 Feb. 2018, which is a division of U.S. patent application Ser. No. 12/971,645, filed 17 Dec. 2010 (the '645 application), now U.S. Pat. No. 8,814,857, issued 26 Aug. 2014. The '574 application, '823 application and the '645 application are each hereby incorporated by reference as though fully set forth herein.

BACKGROUND OF THE INVENTION a. Field of the Invention

The instant disclosure relates generally to ablation electrode assemblies. In particular, the instant disclosure relates to ablation electrode assemblies having a mechanism for irrigating the ablation electrode assemblies and/or targeted tissue areas in a human body. The instant disclosure further relates to irrigated ablation electrode assemblies that include an electrode having at least one radially extending passageway for irrigation fluid. In an embodiment, the instant disclosure further relates to irrigated ablation electrode assemblies that include first and second thermally insulating manifolds that will thermally isolate the ablation electrode from the irrigation fluid.

b. Background Art

Electrophysiology catheters are used in a variety of diagnostic and/or therapeutic medical procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

A medical procedure in which an electrophysiology catheter is used includes a first diagnostic catheter deployed through a patient's vasculature to a patient's heart or a chamber or vein thereof. An electrophysiology catheter that carries one or more electrodes can be used for cardiac mapping or diagnosis, ablation and/or other therapy delivery modes, or both. Once at the intended site, treatment can include radio frequency (RF) ablation, cryoablation, laser ablation, chemical ablation, high-intensity focused ultrasound-based ablation, microwave ablation, etc. An electrophysiology catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents stray errant conduction signals that can form the basis for arrhythmias.

Because RF ablation can generate significant heat, which if not controlled can result in excessive tissue damages, such as steam pop, tissue charring, and the like, it can be desirable to monitor the temperature of ablation electrode assemblies. It can also be desirable to include a mechanism to irrigate the ablation electrode assemblies and/or targeted areas in a patient's body with biocompatible fluids, such as saline solution. The use of irrigated ablation electrode assemblies can also prevent the formation of soft thrombus and/or blood coagulation, as well as enable deeper and/or greater volume lesions as compared to conventional, non-irrigated catheters at identical power settings.

Typically, there are two classes of catheters incorporating irrigated ablation electrode assemblies: open and closed irrigation catheters. Closed irrigation catheters usually circulate a cooling fluid within an inner cavity of the electrode. Open irrigation catheters usually deliver the cooling fluid through open outlets or openings on the surface of the electrode. Open irrigation catheters use the inner cavity of the electrode, or distal member, as a manifold to distribute saline solution, or other biocompatible irrigation fluids known to those of ordinary skill in the art, to one or more passageways that lead to openings/outlets provided on the surface of the electrode. The saline solution (or other biocompatible irrigation fluid) thus flows directly through the outlets of the passageways onto the electrode or distal member. The direct flow of fluid through the electrode can lower the temperature of the distal end of the electrode during operation, rendering accurate monitoring and control of the ablation more difficult.

Some open irrigation catheters can include a thermally insulating manifold made of a reduced thermally conductive material, such as plastic, for example to enable more accurate monitoring and control of the ablation. Although the use of a thermally insulating manifold made of a reduced thermally conductive material can be beneficial, such a thermally insulating manifold can be generally difficult to manufacture and the resulting structures can cause reliability issues.

BRIEF SUMMARY OF THE INVENTION

It is desirable to be able to provide irrigated ablation electrode assemblies that have improved manufacturability and reliability.

The instant disclosure relates to an irrigated ablation electrode assembly comprising a distal member, a first manifold, and a second manifold in accordance with a first embodiment. The distal member includes an outer surface, an inner surface, and at least one radially extending passageway that extends from the inner surface of the distal member to the outer surface of the distal member. The distal member can include a plurality of radially extending passageways. At least a portion of at least one of the plurality of radially extending passageways can include a coating comprised of an electrically non-conductive material in an embodiment of the disclosure. The distal member can be comprised of an electrically conductive material. A thermal sensor can be disposed within the distal member.

The first manifold includes an outer surface, an inner cavity, and at least one radially extending passageway that extends from the inner cavity to the outer surface of the first manifold. The first manifold can include a plurality of radially extending passageways. The first manifold can be a thermal insulator having reduced thermal conductivity. At least a portion of the first manifold can be disposed internally relative to at least a portion of the distal member. The first manifold can further include an axially extending passageway extending from the inner cavity to a distal end of the first manifold. At least a portion of an end of each of the plurality of radially extending passageways and at least a portion of an end of the axially extending passageway can be located at approximately the same position along a longitudinal axis of the ablation electrode assembly.

The second manifold includes an outer surface, an inner surface, and at least one radially extending passageway that extends from the inner surface of the second manifold to the outer surface of the second manifold. The second manifold can include a plurality of radially extending passageways. The second manifold can be a thermal insulator having reduced thermal conductivity. At least a portion of the second manifold can be disposed externally relative to at least a portion of the distal member. The at least one radially extending passageway of the first manifold, the at least one radially extending passageway of the second manifold, and the at least one radially extending passageway of the distal member can be radially aligned.

A plate can be mounted inside at least one of the radially extending passageway of the first manifold, the radially extending passageway of the second manifold, or the radially extending passageway of the distal member. The plate includes an aperture for metering fluid flow.

The instant disclosure also relates to an irrigated catheter assembly comprising a catheter including a catheter shaft having a fluid lumen and an irrigation ablation electrode assembly.

The instant disclosure also relates to an irrigated ablation electrode assembly comprising a distal member, a first manifold, and a second manifold in accordance with a second embodiment. In accordance with the second embodiment, the second manifold can comprise a first portion comprising a generally annular ring with a first outer diameter. The least one radially extending passageway can be disposed in the first portion. The second manifold can further comprise a second portion comprising a radially outwardly extending flange with a second outer diameter. The second outer diameter can be greater than the first outer diameter. In accordance with the second embodiment, the irrigated ablation electrode assembly can further include a flow member. The flow member can comprise a generally annular ring having a proximal end and a distal end. The proximal end of the flow member can engage the distal member. The distal end of the flow member can define a circumferential irrigation port between the flow member and the second manifold.

The instant disclosure also relates to an irrigated ablation electrode assembly comprising a distal member in accordance with a third embodiment. In accordance with the third embodiment, the distal member has a distal end and a proximal end. The distal member comprises a body and a cap. The body has a distal portion and a proximal portion. The distal portion has a larger outer diameter than the proximal portion. The distal portion defines a bore and defines at least one substantially axially extending port. The cap has a first portion and a second portion. The first portion of the cap is disposed within the bore of the body. The second portion of the cap extends outside the body. The second portion of the cap includes at least one radially extending port. The distal member can include at least one axially extending port configured to receive a thermal sensor.

The foregoing and other aspects, features, details, utilities, and advantages of the present disclosure will be apparent from reading the following description and claims, and from reviewing the accompanying drawings.

DETAILED DESCRIPTION OF THE DISCLOSURE

The instant disclosure generally relates to irrigated ablation electrode assemblies. For purposes of this description, similar aspects among the various embodiments described herein will be referred to by the same reference number. As will be appreciated, however, the structure of the various aspects can be different among the various embodiments.

Figure 1:
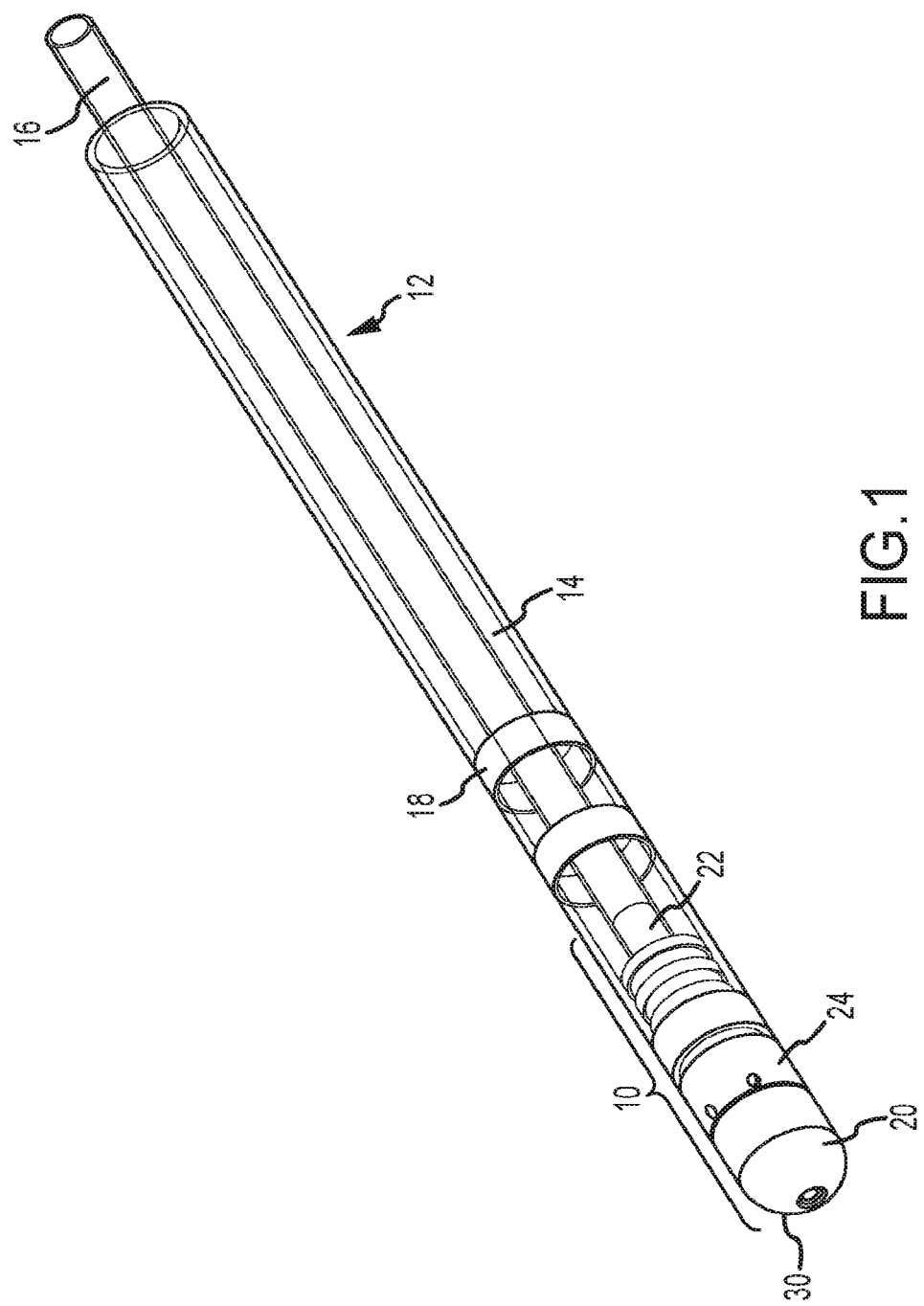
FIG. 1 is an isometric partially transparent view of an irrigation catheter incorporating an irrigated ablation electrode assembly in accordance with a first embodiment of the disclosure.

As generally shown in the embodiment illustrated in FIG. 1, the ablation electrode assembly 10 can comprise part of an irrigated catheter assembly 12. Irrigated catheter assembly 12 can be provided for examination, diagnosis, and/or treatment of internal body tissues (e.g., targeted tissue areas). In an exemplary embodiment, irrigated catheter assembly 12 can comprise an ablation catheter (e.g., radio frequency (RF), cryoablation, ultrasound, etc.). The instant disclosure generally refers to RF ablation electrodes and assemblies, but it is contemplated that the instant disclosure is equally applicable to any number of other ablation electrodes and assemblies where the temperature of the device and the targeted tissue areas can be factors during diagnostic and/or therapeutic medical procedures.

Irrigated catheter assembly 12 includes a catheter shaft 14 having a proximal end and a distal end. The catheter shaft 14 is an elongate, tubular, flexible member configured for movement within a body. The catheter shaft 14 can be introduced into a blood vessel or other structure within a body through a conventional introducer. The catheter shaft 14 can be steered or guided through a body to a desired location such as targeted tissue areas with pullwires, tension elements, so-called push elements, or other means known in the art.

Irrigated catheter assembly 12 further includes at least one fluid lumen or fluid delivery tube 16 disposed within the catheter shaft 14. The fluid delivery tube 16 is configured to supply fluid to the ablation electrode assembly 10. The fluid delivery tube 16 of the irrigated catheter assembly 12 can be connected to a fluid source (not shown) providing a biocompatible fluid such as saline, or a medicament, through a pump (not shown), which can comprise, for example, a fixed rate roller pump or variable volume syringe pump with a gravity feed supply from the fluid source for irrigation. The fluid source and/or pump is conventional in the art. The fluid source and/or pump can comprise a commercially available unit sold under the name Cool Point™, available from St. Jude Medical, Inc. in an embodiment.

Irrigated catheter assembly 12 further includes one or more electrodes 18 mounted in or on the catheter shaft 14. Electrodes 18 can comprise ring electrodes. Electrodes 18 can comprise positioning electrodes used, for example, with a visualization, navigation, and mapping system (not shown). Electrodes 18 can be configured to provide a signal indicative of both a position and orientation of at least a portion of the catheter shaft 14. The visualization, navigation, and/or mapping system with which the electrodes 18 can be used can comprise an electric field-based system, such as, for example, that having the model name ENSITE NAVX (aka EnSite Classic as well as newer versions of the EnSite system, denoted as ENSITE VELOCITY) and commercially available from St. Jude Medical, Inc. and as generally shown with reference to U.S. Pat. No. 7,263,397 titled "Method and Apparatus for Catheter Navigation and Location and Mapping in the Heart," the entire disclosure of which is incorporated herein by reference. In accordance with an electric field-based system, the electrodes 18 can be configured to be responsive to an electric field transmitted within the body of the patient. The electrodes 18 can be used to sense an impedance at a particular location and transmit a representative signal to an external computer or processor. In other exemplary embodiments, however, the visualization, navigation, and/or mapping system can comprise other types of systems, such as, for example and without limitation: a magnetic field-based system such as the CARTO System (now in a hybrid form with impedance- and magnetically-driven electrodes) available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd. of Haifa, Israel (now owned by St. Jude Medical, Inc.), and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference. In accordance with a magnetic field-based system, the electrodes 18 can be configured to be responsive to a magnetic field transmitted through the body of the patient. The electrodes 18 can be used to sense the strength of the field at a particular location and transmit a representative signal to an external computer or processor. The electrodes 18 can comprise one or more metallic coils located on or within the catheter shaft 14 in a magnetic field-based system. As noted above, a combination electric field-based and magnetic field-based system such as the CARTO 3 System also available from Biosense Webster, and as generally shown with reference to U.S. Pat. No. 7,536,218 entitled "Hybrid Magnetic-Based and Impedance-Based Position Sensing," the entire disclosure of which is incorporated herein by reference, can be used. In accordance with a combination electric field-based and magnetic field-based system, the electrodes 18 can comprise both one or more impedance-based electrodes and one or more magnetic coils. Commonly available fluoroscopic, computed tomography (CT), and magnetic resonance imaging (MRI)-based systems can also be used.

Irrigated catheter assembly 12 can include other conventional components such as, for example and without limitation, conductors associated with the electrodes 18, and possibly additional electronics used for signal processing, visualization, localization, and/or conditioning. Irrigated catheter assembly 12 can further include multiple lumens for receiving additional components. Irrigated catheter assembly 12 can further include a cable connector or interface (not shown) and a handle (not shown). The cable connector or interface can provide mechanical, fluid, and electrical connection(s) for cables (not shown) extending from the pump and/or an ablation system as described in more detail below. The cable connector or interface can be conventional in the art and can be disposed at the proximal end of the irrigated catheter assembly 12. The handle can provide a location for the clinician to hold the irrigated catheter assembly 12 and can further provide means for steering or guiding the catheter shaft 14 within the body as known in the art. Catheter handles are generally conventional in the art and it will be understood that the construction of the handle can vary. In an embodiment, for the purpose of steering the catheter shaft 14 within the body, the handle can be substituted by a controllable robotic actuator.

Ablation electrode assembly 10 can be connected to and/or coupled with catheter shaft 14 to form irrigated catheter assembly 12. Referring now to FIGS. 1-5, the ablation electrode assembly 10 of irrigated catheter assembly 12 can include a distal member 20, a first manifold 22, and a second manifold 24 in accordance with a first embodiment of the disclosure. The lengths and/or diameters of distal member 20, first manifold 22, and second manifold 24, ablation electrode assembly 10, as well as portions thereof, can vary depending on the design of ablation electrode assembly 10. The distal member 20 may be about 4 millimeters in length in an embodiment.

Distal member 20 can be disposed at or near the distal end of catheter shaft 14. Distal member 20 can be disposed at the extreme distal end (e.g., tip) of the shaft 14. Distal member 20 can be comprised of any electrically, and potentially thermally, conductive material known to those of ordinary skill in the art for the delivery of ablative energy to targeted tissue areas. Examples of electrically conductive materials include gold, platinum, iridium, palladium, stainless steel, and/or any combination thereof. In particular, a combination of platinum and iridium can be used in various combinations. Accordingly, in an embodiment, distal member 20 is an ablation electrode for use in RF ablation.

Figure 3:
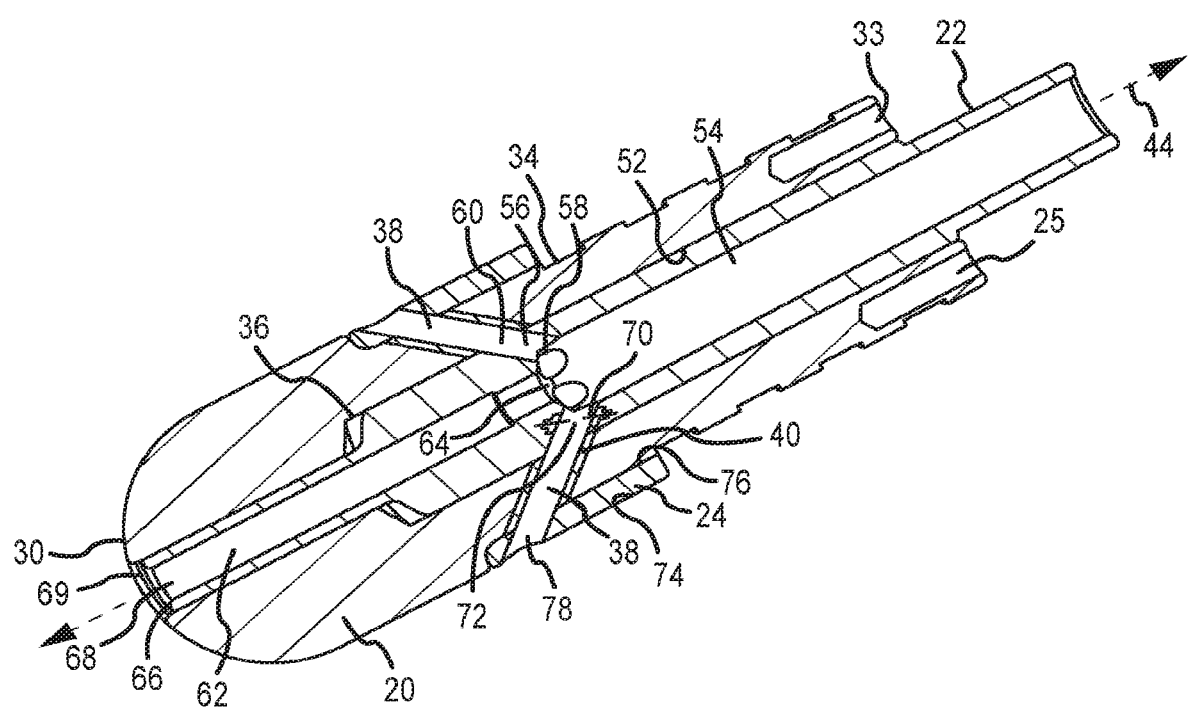
FIG. 3 is an isometric cross-sectional view of the irrigated ablation electrode assembly of FIG. 1.

Distal member 20 can be electrically connected to an ablation system (not shown) to allow for the delivery of ablative energy, or the like. Distal member 20 can be electrically connected to an ablation system in any manner conventional in the art. For example, a power wire 25 can be provided within distal member 20 of ablation electrode assembly 10 as generally illustrated in FIG. 3. The power wire 25 can extend through a lumen(s) provided within the ablation electrode assembly 10. Irrigated catheter assembly 12 can be configured for operation at an initial power setting of up to 50 Watts. The ablation system can be comprised of, for example, an ablation generator (not shown) and one or more ablation patch electrodes (not shown). The ablation generator generates, delivers, and controls ablation energy (e.g., RF) output by the irrigated catheter assembly 12 and the distal member 20 thereof, in particular. The generator is conventional in the art and can comprise a commercially available unit sold under the model number IBI-1500T RF Cardiac Ablation Generator, available from St. Jude Medical, Inc. In an exemplary embodiment, the generator can include an RF ablation signal source configured to generate an ablation signal that is output across a pair of source connectors: a positive polarity connector SOURCE (+), which electrically connects to the distal member 20 of the ablation electrode assembly 10 of the irrigated catheter assembly 12; and a negative polarity connector SOURCE (−), can be electrically connected to one or more of the patch electrodes. It should be understood that the term connectors as used herein does not imply a particular type of physical interface mechanism, but is rather broadly contemplated to represent one or more electrical nodes (including multiplexed and de-multiplexed nodes). The source is configured to generate a signal at a predetermined frequency in accordance with one or more user specified control parameters (e.g., power, time, temperature, etc.) and under the control of various feedback sensing and control circuitry. The source can generate a signal, for example, with a frequency of about 450 kHz or greater for RF energy. The generator can also monitor various parameters associated with the ablation procedure including, for example, impedance, the temperature at the distal tip of the irrigated catheter assembly, applied ablation energy, power, force, proximity, and the position of the irrigated catheter assembly, and provide feedback to the clinician or another component within the irrigated catheter assembly regarding these parameters. Operation in a temperature control mode can be at a set point above 50 degrees Celsius.

Figure 2:
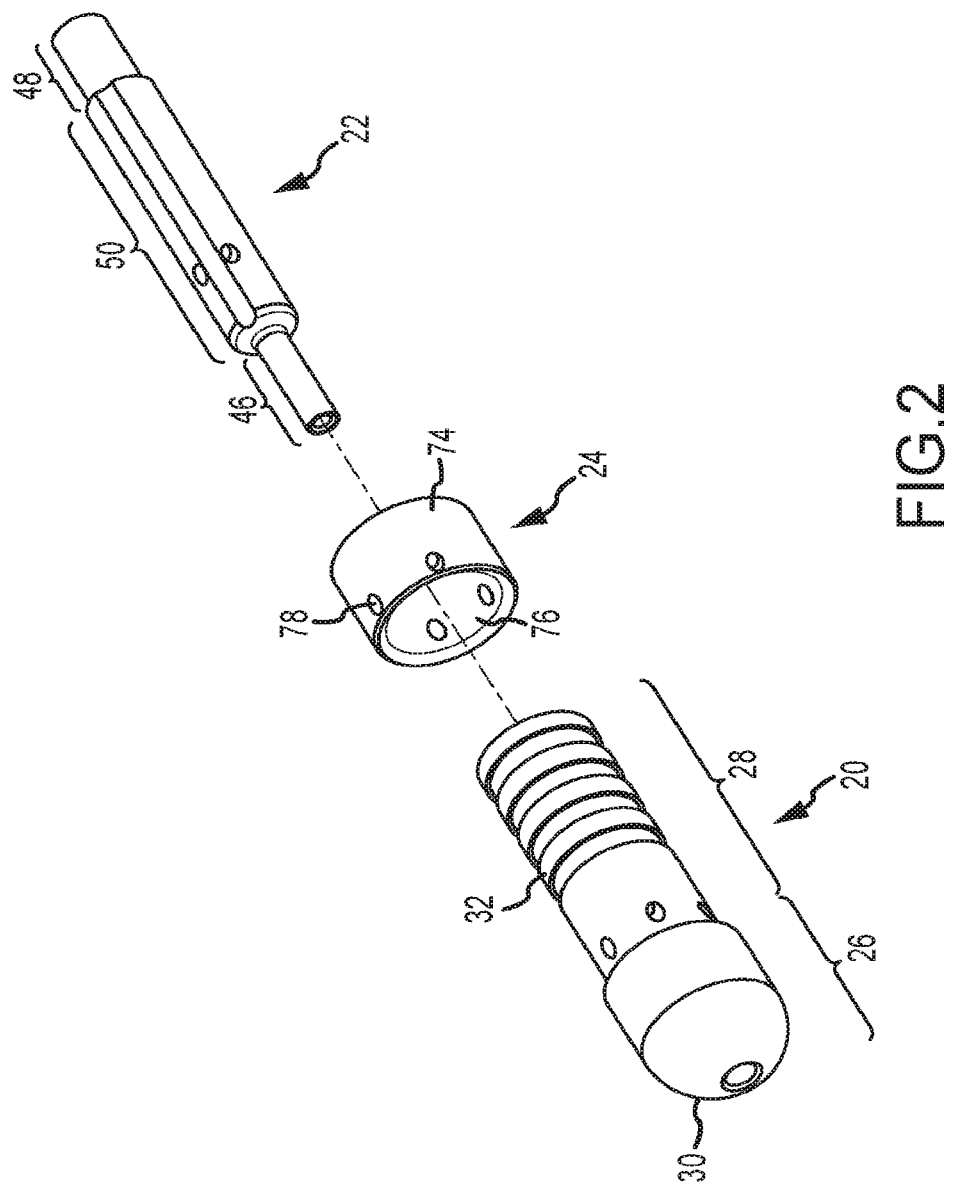
FIG. 2 is an isometric exploded view of the irrigated ablation electrode assembly of FIG. 1.

As best illustrated in FIG. 2, distal member 20 can include a distal end portion 26 and a proximal end portion 28. Distal end portion 26 of distal member 20 can be generally cylindrical in shape and can include a distal end or tip 30. Distal end 30 of distal end portion 26 can be partially spherical or hemispherical in shape in accordance with an embodiment of the disclosure. Proximal end portion 28 of distal member 20 can also be generally cylindrical in shape. Proximal end portion 28 can have a reduced diameter relative to a diameter of the distal end portion 26. At least a portion of proximal end portion 28 can include a plurality of radially outwardly extending threads 32. Proximal end portion 28 of distal member 20 can be configured for coupling and/or connecting distal member 20 with catheter shaft 14. At least one retaining wire 33 can be connected to distal member 20 as generally illustrated in FIG. 3. Retaining wire 33 can be configured to ensure that distal member 20 and/or ablation electrode assembly 10 is not separated from catheter shaft 14 during movement of irrigated catheter assembly 12 within a body.

As best illustrated in FIG. 3, distal member 20 also has an outer surface 34, an inner surface 36, and at least one radially extending passageway 38 that extends from the inner surface 36 of the distal member 20 to the outer surface 34 of the distal member 20. Distal member 20 includes a plurality of radially extending passageways 38 in an embodiment. Each of the radially extending passageways 38 of the distal member 20 extend from the inner surface 36 of the distal member 20 to the outer surface 34 of the distal member 20. Each of the radially extending passageways 38 of the distal member 20 can be disposed within the proximal portion 28 of the distal member 20 in an embodiment. In an embodiment, the radially extending passageways 38 of the distal member 20 are oriented and/or angled generally toward distal end or tip 30 at an acute angle (e.g., between about 20 to about 70 degrees, and for some embodiments, between about 30 to about 65 degrees) with respect to the longitudinal axis 44 of the ablation electrode assembly 10. The orientations of the radially extending passageways 38 vary depending on the design of the ablation electrode assembly 10. The radially extending passageways 38 of the distal member 20 can be straight or curved in various embodiments of the disclosure. The radially extending passageways 38 of the distal member 20 can be substantially equally spaced around the perimeter or circumference of the distal member 20 in accordance with an embodiment of the disclosure. Substantially equal spacing of the radially extending passageways 38 of the distal member 20 can provide substantially equal distribution of irrigation fluid (e.g., saline) to the targeted tissue areas and/or the outside of ablation electrode assembly 10. The radially extending passageways 38 of the distal member 20 can be generally tubular and can have a constant diameter along their length. In an embodiment, radially extending passageways 38 of the distal member 20 can have a diameter ranging in size from about 0.008 to about 0.015 inches, and for some embodiments between about 0.010 to about 0.012 inches. Alternate configurations having various shapes and diameters, for example, along all or portions of the length of the radially extending passageways 38 can be used in various embodiments.

In an embodiment of the disclosure, a casing or coating 40 can be disposed on at least a portion of the distal member 20 that defines at least one of the plurality of the radially extending passageways 38. The coating 40 can be comprised of an electrically non-conductive material. The coating 40 can be comprised of diamond, diamond-like carbon or polytetrafluoroethylene, which is commonly sold by the E. I. du Pont de Nemours and Company under the trade name Teflon®. In an embodiment, coating 40 is provided around the entire circumference and along the entire length of least one of the plurality of the radially extending passageways 38. However, coating 40 can be provided only around a portion of the circumference and/or only around a portion of the length of at least one of the plurality of the radially extending passageways 38 in accordance with various embodiments of the disclosure. The amount of coating 40 provided around the circumference and/or length of at least one of the plurality of the radially extending passageways 38 can vary depending on the relative requirements of ablation electrode assembly 10.

Figure 4:
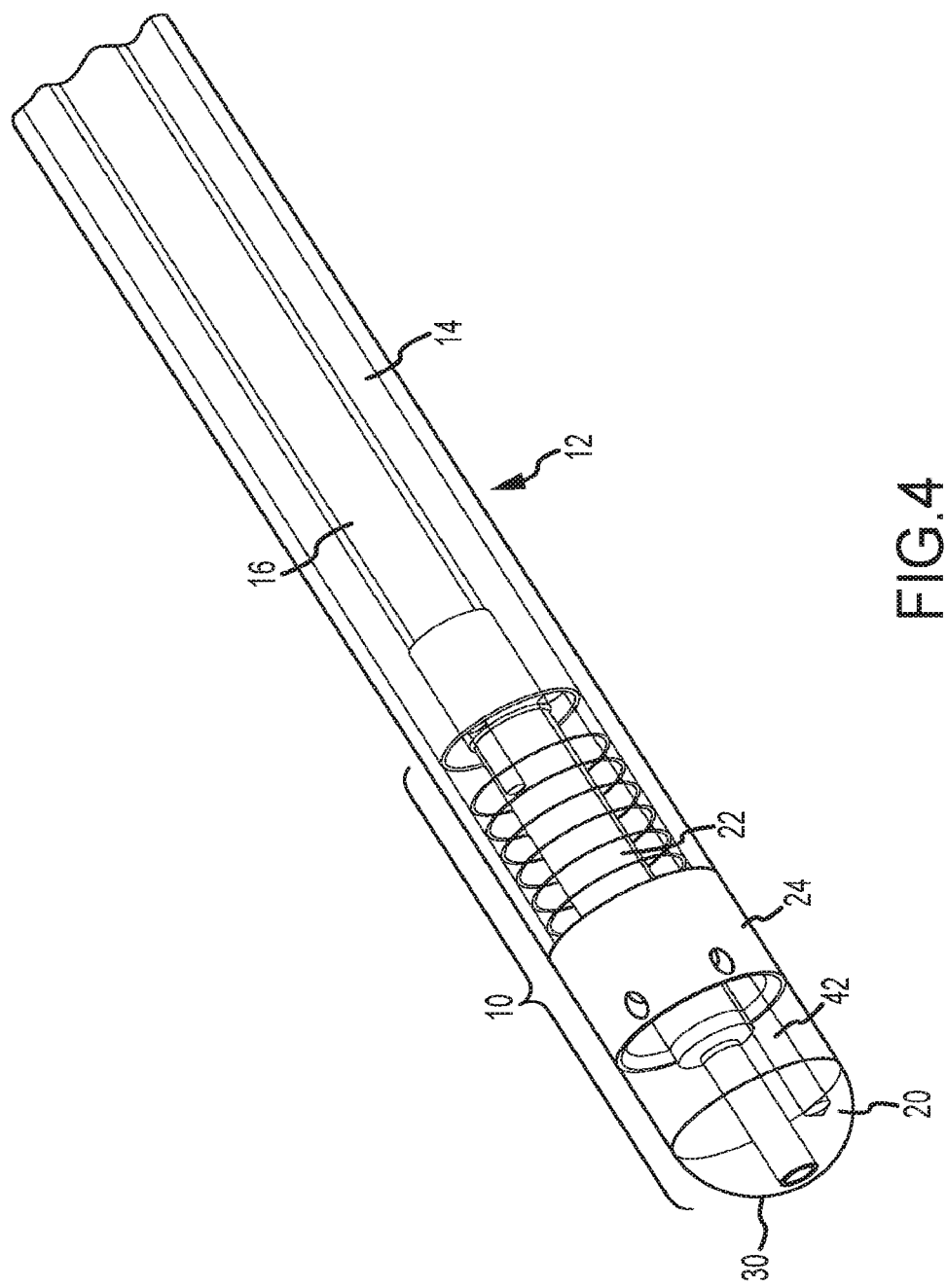
FIG. 4 is an isometric partially transparent view of the irrigation catheter and of the irrigated ablation electrode assembly of FIG. 1.
Figure 5:
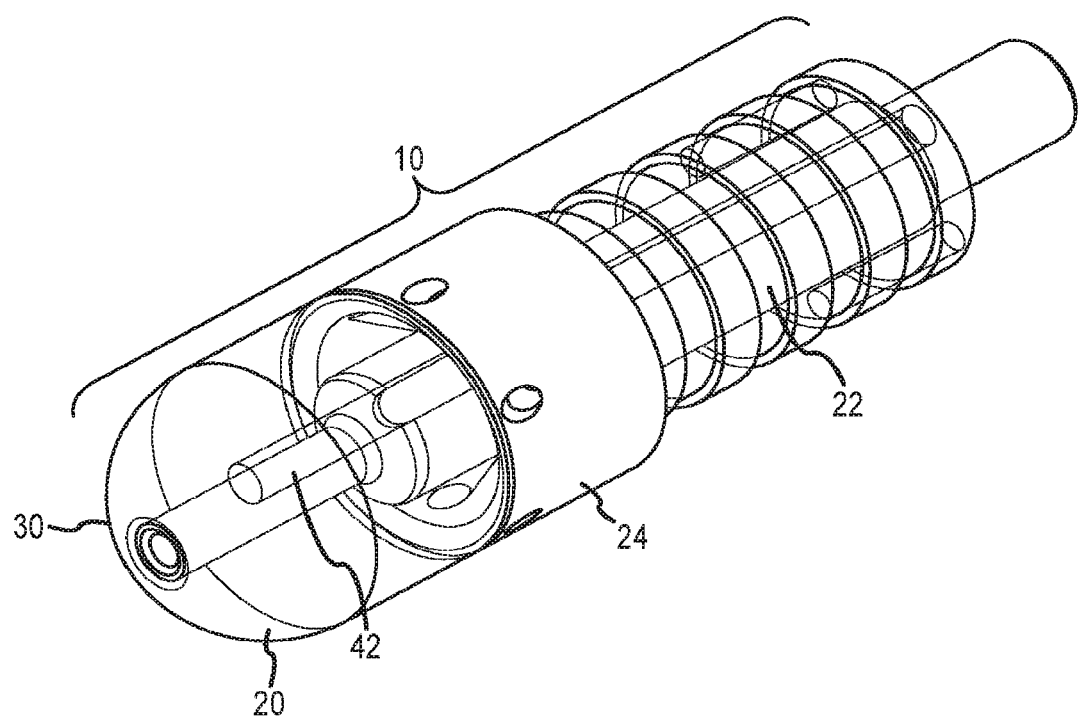
FIG. 5 is an isometric partially transparent view of the irrigated ablation electrode assembly of FIG. 1.

Distal member 20 can include one or more additional lumens for receiving additional components of the ablation electrode assembly 10. For example, distal member 20 can include at least one lumen for receiving a temperature sensing mechanism 42 as generally illustrated in FIG. 4. The temperature sensing mechanism 42 can be configured for measurement and temperature control/regulation of ablation electrode assembly 10. The temperature sensing mechanism 42 can be any mechanism known to one of ordinary skill in the art, including for example and without limitation, thermal sensors, thermocouples, and/or thermistors. In an embodiment, the temperature sensing mechanism 42 can be surrounded and/or encapsulated by a thermally conductive and electrically non-conductive material (not shown). The thermally conductive and electrically non-conductive material can serve to hold temperature sensing mechanism 42 in place within distal member 20 and/or provide improved heat exchange between temperature sensing mechanism 42 and distal member 20. The thermally conductive and electrically non-conductive material can be comprised of a number of materials known to one of ordinary skill in the art, including for example, thermally conductive resins, epoxies, or potting compounds.

First manifold 22 and distal member 20 can be serially coupled together or connected with one another along the same longitudinal axis 44. First manifold 22 and distal member 20 can be connected or coupled together by any known mechanisms including, for example and without limitation, adhesives, press-fit configurations, snap-fit configurations, or any other mechanism known to one of ordinary skill in the art. First manifold 22 is provided to isolate the distal member 20 from the irrigation fluid (e.g., saline) that can be used during a diagnostic and/or therapeutic medical procedure. The first manifold 22 is a thermal insulator having a reduced thermal conductivity. The first manifold 22 can be thermally nonconductive in accordance with an embodiment of the disclosure. Moreover, the first manifold 22 can comprise an electrically nonconductive material in accordance with an embodiment of the disclosure. In general, the first manifold 22 is lower in thermal conductivity, and preferably substantially lower, than distal member 20. First manifold 22 can comprise a reduced thermally conductive polymer in accordance with an embodiment of the disclosure. A reduced thermally conductive polymer is one with physical attributes that decrease heat transfer by about 10% or more, provided that the remaining structural components are selected with the appropriate characteristics and sensitivities desired for the ablation electrode assembly 10. One reduced thermally conductive material can include polyether ether ketone (PEEK). Additional examples of thermally nonconductive or reduced thermally conductive materials that can be useful in conjunction with the instant disclosure include, but are not limited to, high density polyethylene (HDPE), polyimide thermoplastic resins, such as ULTEM® as provided by General Electric Plastics (now known as SABIC Innovative Plastics), polyaryletherketones, polyurethane, polypropylene, oriented polypropylene, polyethylene, crystallized polyethylene terephthalate, polyethylene terephthalate, polyester, polyetherimide, acetyl, ceramics, and/or various combinations thereof. First manifold 22 can also comprise other plastic materials such as silicone or polyether block amides such as those sold under the trademark PEBAX® and generally available from Arkema France in other embodiments of the disclosure.

As best illustrated in FIG. 2, first manifold 22 can include a distal end portion 46, a proximal end portion 48, and an intermediate portion 50. Distal end portion 46 can be generally cylindrical in shape. Proximal end portion 48 can also be generally cylindrical in shape. Proximal end portion 48 can have a larger diameter relative to a diameter of the distal end portion 46. Intermediate portion 50 can also be generally cylindrical in shape. Intermediate portion 50 can have a larger diameter relative to both a diameter of the distal end portion 46 and a diameter of the proximal end portion 48. The inner surface 36 of distal member 20 can define a cavity that is configured to receive at least a portion of first manifold 22. For example and without limitation, the cavity defined by the inner surface 36 of distal member 20 can receive distal end portion 46 and intermediate portion 50 of first manifold 22. Accordingly, at least a portion (e.g., distal end portion 46 and intermediate portion 50) of first manifold 22 can be disposed internally relative to at least a portion of the distal member 20. Proximal end portion 48 can be configured to receive and/or envelop fluid delivery tube 16 carried within the catheter shaft 14.

As best illustrated in FIG. 3, first manifold 22 has an outer surface 52, an inner cavity 54, and at least one radially extending passageway 56 that extends from the inner cavity 54 to the outer surface 52 of the first manifold 22. First manifold 22 includes a plurality of radially extending passageways 56 in an embodiment.

Each of the radially extending passageways 56 of the first manifold 22 extend from the inner cavity 54 of the first manifold 22 at a first end 58 of each of the radially extending passageways 56 to the outer surface 52 of the first manifold 22 at a second end 60 of each of the plurality of the radially extending passageways 56. Each of the radially extending passageways 56 of the first manifold 22 can be disposed within the intermediate portion 50 of the first manifold 22 in an embodiment. In an embodiment, the radially extending passageways 56 of the first manifold 22 are oriented and/or angled generally toward distal end or tip 30 at an acute angle (e.g., between about 20 to about 70 degrees, and for some embodiments, between about 30 to about 65 degrees) with respect to the longitudinal axis 44 of the ablation electrode assembly 10. The orientations of the radially extending passageways 56 vary depending on the design of the ablation electrode assembly 10. The radially extending passageways 56 of the first manifold 22 can be straight or curved in various embodiments of the disclosure. The radially extending passageways 56 of the first manifold 22 can be substantially equally spaced around the perimeter or circumference of the first manifold 22 in accordance with an embodiment of the disclosure. Substantially equal spacing of the radially extending passageways 56 of the first manifold 22 can provide substantially equal distribution of irrigation fluid (e.g., saline) to the targeted tissue areas and/or the outside of ablation electrode assembly 10. The radially extending passageways 56 of the first manifold 22 can be generally tubular and can have a constant diameter along their length. In an embodiment, radially extending passageways 56 of the first manifold 22 can have a diameter ranging in size from about 0.008 to about 0.015 inches, and for some embodiments between about 0.010 to about 0.012 inches. Alternate configurations having various shapes and diameters, for example, along all or portions of the length of the radially extending passageways 56 can be used in various embodiments.

The first manifold 22 further comprises an axially extending passageway 62 extending from the inner cavity 54 at a first end 64 of the axially extending passageway 62 to a distal end 66 of the first manifold 22 at a second end 68 of the axially extending passageway 62 in some embodiments. The axially extending passageway 62 enables irrigation fluid to flow to distal end or tip 30 of distal member 20 and through a distal tip port 69, therein substantially irrigating the tip 30 of the distal member 20 of the ablation electrode assembly 10. The axially extending passageway 62 and/or the distal tip port 69 is optional, such that the radially extending passageways 56 of the first manifold 22 can be the only source of irrigation fluid in some embodiments of the disclosure. In such embodiments of the disclosure, the only source of irrigation fluid is from the periphery of the ablation electrode assembly 10 proximal of the distal member 20. In such embodiments of the disclosure, the distal member 20 can comprise, for example and without limitation, a solid electrode (e.g., a solid metallic electrode) or a two-piece electrode comprising a cap over a core (e.g., a metallic cap over a core of a resin-based material). At least a portion of the first end 58 of each of the plurality of radially extending passageways 56 of the first manifold 22 and at least a portion of the first end 64 of the axially extending passageway 62 of the first manifold 22 are located at approximately the same position along a longitudinal axis 44 of the ablation electrode assembly 10. By positioning the first ends 58, 64 of all passageways 56, 62 (i.e., both radially extending passageways 56 and axially extending passageway 62) in close proximity, improved fluid flow balance can be achieved. Moreover, the co-location of the first ends 58, 64 of all passageways 56, 62 (i.e., both radially extending passageways 56 and axially extending passageway 62) can reduce the siphoning effect (i.e., reverse flow of blood into the ablation electrode assembly 10) due to local low pressure zones at higher flow rates.

Additional metering control can be achieved by mounting a plate 70 inside at least one of the plurality of the radially extending passageways 62 of the first manifold 22. The plate 70 can include an aperture 72 for metering fluid flow through the radially extending passageway 62. In particular, the plate 70 can be a thin plate with a sharp-edged aperture 72 through which the fluid in the passageway 62 can be accelerated. The acceleration of the fluid flow can cause the local static pressure to decrease. The flow rate can be sensed by taking one pressure reading upstream of the aperture 72 and one pressure reading downstream of the aperture 72. Although a plate 70 is described as being mounted in at least one of the plurality of the radially extending passageways 62 of the first manifold 22, a plate 70 can also be mounted in at least one of the plurality of the radially extending passageways 38 of the distal member 20, and/or at least one of the plurality of the radially extending passageways 78 of the second manifold 24, and/or combinations thereof in accordance with other embodiments of the disclosure. In accordance with an embodiment, overall total fluid volumes can be much lower than prior art or typically utilized in clinical practice, especially valuable for patients already suffering from fluid overload (e.g., patient having heart failure and the like). That is, overall total fluid volume can be below thirteen milliliters per minute while effectively reducing or eliminating char and coagulum and improving temperature correlation for precise control of power to maintain a temperature during ablation procedures.

Second manifold 24, first manifold 22, and distal member 20 can be serially coupled together or connected with one another along the same longitudinal axis 44. Second manifold 24, first manifold 22 and distal member 20 can be connected or coupled together by any known mechanisms including, for example and without limitation, adhesives, press-fit configurations, snap-fit configurations, or any other mechanism known to one of ordinary skill in the art. Second manifold 24 is provided to isolate the distal member 20 from the irrigation fluid (e.g., saline) that can be used during a diagnostic and/or therapeutic medical procedure. The second manifold 24 is a thermal insulator having a reduced thermal conductivity. The second manifold 24 can be thermally nonconductive in accordance with an embodiment of the disclosure. Moreover, the second manifold 24 can comprise an electrically nonconductive material in accordance with an embodiment of the disclosure. In general, the second manifold 24 is lower in thermal conductivity, and preferably substantially lower, than distal member 20. Second manifold 24 can comprise a reduced thermally conductive polymer in accordance with an embodiment of the disclosure. One reduced thermally conductive material can include PEEK. Additional examples of thermally nonconductive or reduced thermally conductive materials that can be useful in conjunction with the instant disclosure include, but are not limited to, HDPE, polyimide thermoplastic resins, such as ULTEM® as provided by General Electric Plastics (now known as SABIC Innovative Plastics), polyaryletherketones, polyurethane, polypropylene, oriented polypropylene, polyethylene, crystallized polyethylene terephthalate, polyethylene terephthalate, polyester, polyetherimide, acetyl, ceramics, and/or various combinations thereof. Second manifold 24 can also comprise other plastic materials such as silicone or polyether block amides such as those sold under the trademark PEBAX® and generally available from Arkema France in other embodiments of the disclosure.

As best illustrated in FIG. 2, second manifold 24 can comprise a generally annular ring. An outer diameter of the generally annular ring comprising second manifold 24 can be substantially the same as an outer diameter of the distal end portion 26 of distal member 20. As best illustrated in FIGS. 2-3, second manifold 24 has an outer surface 74, an inner surface 76, and at least one radially extending passageway 78 that extends from the inner surface 76 of the second manifold 24 to the outer surface 74 of the second manifold 24.

Second manifold 24 includes a plurality of radially extending passageways 78 in an embodiment. Each of the radially extending passageways 78 of the second manifold 24 extend from the inner surface 76 of the second manifold 24 to the outer surface 74 of the second manifold 24. The radially extending passageways 78 of the second manifold 24 can be substantially equally spaced around the circumference of the second manifold 24 in accordance with an embodiment of the disclosure. In an embodiment, the radially extending passageways 78 of the second manifold 24 are oriented and/or angled generally toward distal end or tip 30 at an acute angle (e.g., between about 20 to about 70 degrees, and for some embodiments, between about 30 to about 65 degrees) with respect to the longitudinal axis 44 of the ablation electrode assembly 10. The orientations of the radially extending passageways 78 vary depending on the design of the ablation electrode assembly 10. The radially extending passageways 78 of the second manifold 24 can be straight or curved in various embodiments of the disclosure. The radially extending passageways 78 of the second manifold 24 can be substantially equally spaced around the perimeter or circumference of the second manifold 24 in accordance with an embodiment of the disclosure. Substantially equal spacing of the radially extending passageways 78 of the second manifold 24 can provide substantially equal distribution of irrigation fluid (e.g., saline) to the targeted tissue areas and/or the outside of ablation electrode assembly 10. The radially extending passageways 78 of the second manifold 24 can be generally tubular and can have a constant diameter along their length. In an embodiment, radially extending passageways 78 of the second manifold can have a diameter ranging in size from about 0.008 to about 0.015 inches, and for some embodiments between about 0.010 to about 0.012 inches. Alternate configurations having various shapes and diameters, for example, along all or portions of the length of the radially extending passageways 78 can be used in various embodiments.

At least a portion of the second manifold 24 is disposed externally relative to at least a portion (e.g., at least a portion of proximal end portion 28) of the distal member 20. For example, the second manifold 24 can surround and/or encircle at least a portion of the distal member 20. When the distal member 20, first manifold 22, and second manifold 24 are assembled, the at least one radially extending passageway 38 of the distal member 20, the at least one radially extending passageway 56 of the first manifold 22, and the at least one radially extending passageway 78 of the second manifold 24 are radially aligned in an embodiment of the disclosure.

Figure 6:
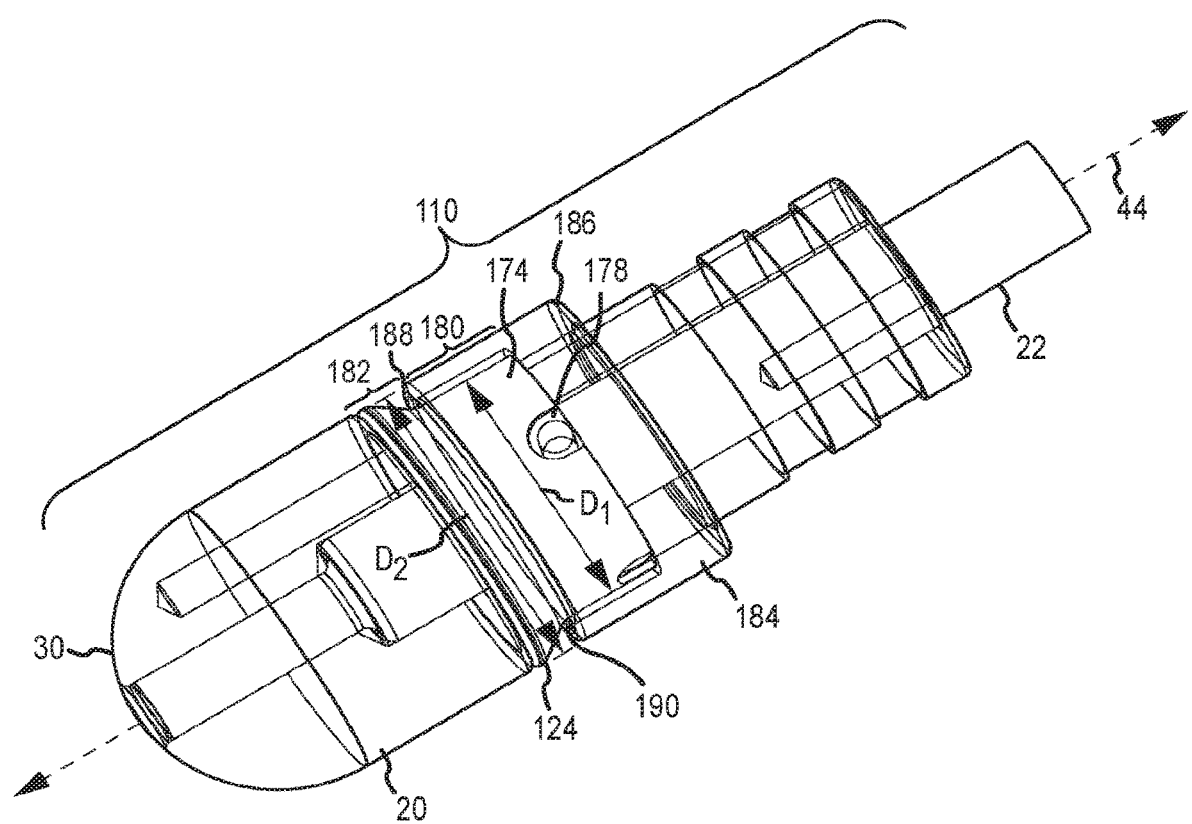
FIG. 6 is an isometric partially transparent view of an irrigated ablation electrode assembly in accordance with a second embodiment of the disclosure.
Figure 7:
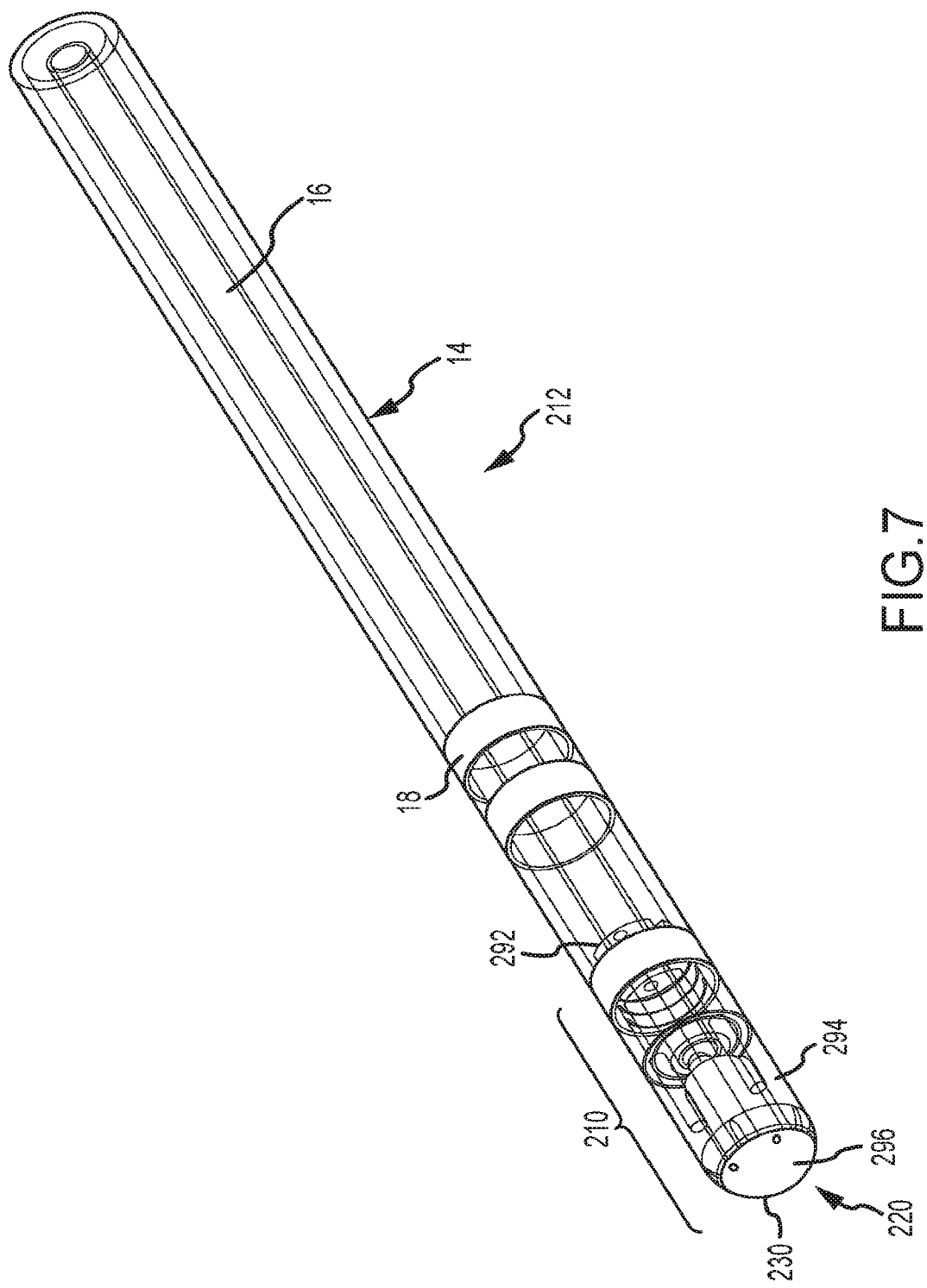
FIG. 7 is an isometric partially transparent view of an irrigation catheter incorporating an irrigated ablation electrode assembly in accordance with a third embodiment of the disclosure.
Figure 8:
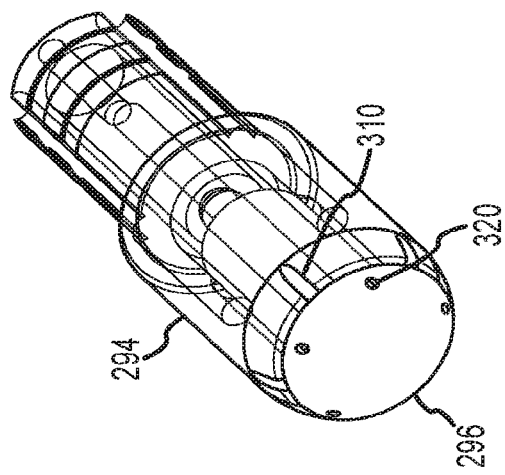
FIG. 8 is an isometric partially transparent view of the irrigated ablation electrode assembly of FIG. 7.
Figure 10:
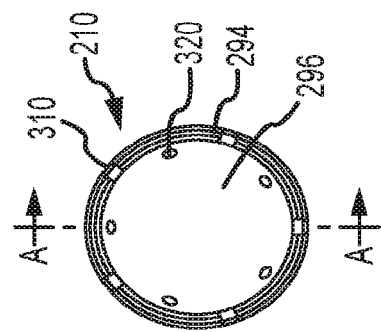
FIG. 10 is a distal end partially transparent view of the irrigated ablation electrode assembly of FIG. 7.
Figure 9:
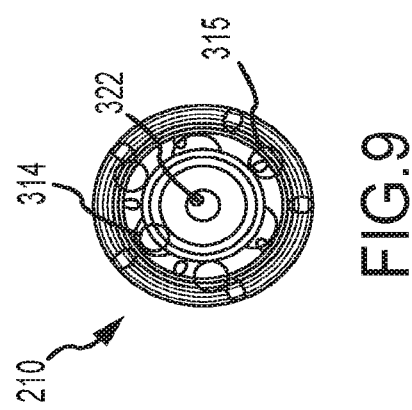
FIG. 9 is a proximal end partially transparent view of the irrigated ablation electrode assembly of FIG. 7.
Figure 11:
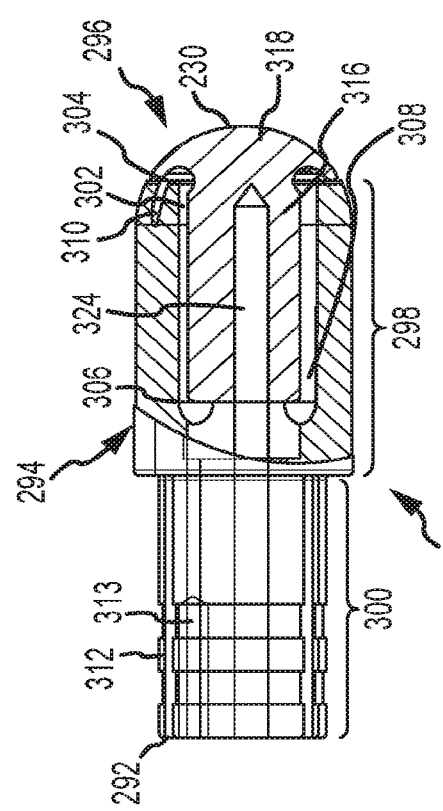
FIG. 11 is a cross-sectional view of the irrigated ablation electrode assembly of FIG. 10, taken along line A-A.

Referring now to FIG. 6, the ablation electrode assembly 110 can include a distal member 20, a first manifold 22, and a second manifold 124 in accordance with a second embodiment of the disclosure. The distal member 20 and first manifold 22 of the ablation electrode assembly 110 in accordance with a second embodiment of the disclosure can be substantially identical to the distal member 20 and first manifold 22 of the ablation electrode assembly 10 as described hereinabove.

The second manifold 124 of the ablation electrode assembly 110 in accordance with a second embodiment of the disclosure can be substantially similar to the second manifold 24 of the ablation electrode assembly 10 as described hereinabove, except that the second manifold 124 includes a first portion 180 and a second portion 182. First portion 180 can be located at a proximal end of the second manifold 124. First portion 180 comprises a generally annular ring with an outer surface 174, an inner surface (not shown), and at least one radially extending passageway 178 that extends from the inner surface of the second manifold 124 to the outer surface 174 of the second manifold 124. First portion 180 of the second manifold 124 has a first outer diameter $D_1$. First outer diameter $D_1$ is smaller than an outer diameter of the distal end portion 26 of distal member 20. First portion 180 of the second manifold 124 is configured to surround and/or encircle proximal end portion 28 of distal member 20. Second portion 182 can be located at a distal end of the second manifold 124. Second portion 182 comprises a radially outwardly extending flange with a second outer diameter $D_2$. The radially outwardly extending flange comprising the section portion 182 of the second manifold 124 can be angled toward the distal end or tip 30 at an acute angle with respect to the longitudinal axis 44 of the ablation electrode assembly 110. The second outer diameter $D_2$ is greater than the first outer diameter $D_1$. Second outer diameter $D_2$ can be substantially the same as an outer diameter of the distal end portion 26 of distal member 20. Second portion 182 of the second manifold 124 is configured to engage the distal end portion 26 of distal member 20.

In accordance with the ablation electrode assembly 110 in accordance with a second embodiment of the disclosure, the ablation electrode assembly 110 further includes a flow member 184. Flow member 184 comprises a generally annular ring having a proximal end 186 and a distal end 188. At least a portion of the proximal end 186 of the flow member 184 can engage the proximal end portion 28 of the distal member 20. At least a portion of the distal end 188 of the flow member 184 can surround and/or encircle second manifold 124 and, further, can define a circumferential irrigation port 190 between the flow member 184 and the second manifold 124. The circumferential irrigation port 190 can be continuous around the entire circumference of the flow member 184 in accordance with an embodiment of the disclosure.

Referring now to FIGS. 7-11, the ablation electrode assembly 210 can include a distal member 220 in accordance with a third embodiment of the disclosure. Ablation electrode assembly 210 can be connected to and/or coupled with catheter shaft 14 to form irrigated catheter assembly 212. Distal member 220 can be disposed at or near the distal end of catheter shaft 14. Distal member 220 can be disposed at the extreme distal end (e.g., tip) of the shaft 14. Distal member 220 has a distal end 230 and a proximal end 292.

Distal member 220 comprises a body 294 and a cap 296. Body 294 of distal member 200 can be comprised of any electrically, and potentially thermally, conductive material known to those of ordinary skill in the art for the delivery of ablative energy to targeted tissue areas. Examples of electrically conductive materials include gold, platinum, iridium, palladium, stainless steel, and/or any combination thereof. In particular, a combination of platinum and iridium can be used in various combinations. Body 294 has a distal portion 298 and a proximal portion 300. Distal portion 298 of body 294 can be generally cylindrical in shape. Distal portion 298 of body 294 defines a blind bore 302. The blind bore 302 is open at a distal end 304 of the distal portion 298 of body 294 and closed at a proximal end 306 of the distal portion 298 of body 294. Distal portion 298 of body 294 also defines at least one axially extending passageway 308 (e.g., fluid distribution channel). The axially extending passageway 308 can extend for substantially the length of the distal portion 298 of body 294. The axially extending passageway 308 can extend to the distal end 304 of the distal portion 298 of body 294. The axially extending passageway 308 enables irrigation fluid to flow to distal end 304 of the distal portion 298 of body 294. The distal portion 298 of body 294 can include at least one proximal irrigation port 310 that is configured to direct irrigation fluid proximally from the axially extending passageway 308. The proximal irrigation port 310 can extend substantially axially relative to the body 294. The distal portion 298 of body 294 can include a plurality of proximal irrigation ports 310 in an embodiment of the disclosure.

Proximal portion 300 of body 294 can be generally cylindrical in shape. Proximal portion 300 of body 294 can have a reduced outer diameter relative to an outer diameter of the distal portion 298 of body 294. At least a portion of proximal portion 300 of body 294 can include a plurality of radially outwardly extending threads 312. Proximal portion 300 of body 294 can be configured for coupling and/or connecting distal member 220 with catheter shaft 14. Body 294 can also include at least one port 314 for receiving a retaining wire 313 that can be configured to ensure that distal member 220 and/or ablation electrode assembly 210 is not separated from catheter shaft 14 during movement of irrigated catheter assembly 212 within a body. Body 294 can also include at least one port 315 for receiving a temperature sensing mechanism (not shown). Body 294 can also include a plurality of ports 315 for receiving temperature sensing mechanisms in accordance with an embodiment of the disclosure. For example and without limitation, body 294 can include three ports 315. The temperature sensing mechanism can be configured for measurement and temperature control/regulation of ablation electrode assembly 210. The temperature sensing mechanism can be any mechanism known to one of ordinary skill in the art, including for example and without limitation, thermal sensors, thermocouples, and/or thermistors.

Cap 296 of distal member 200 can be comprised of any electrically, and potentially thermally, conductive material known to those of ordinary skill in the art for the delivery of ablative energy to targeted tissue areas. Examples of electrically conductive materials include gold, platinum, iridium, palladium, stainless steel, and/or any combination thereof. In particular, a combination of platinum and iridium can be used in various combinations. Cap 296 has a first portion 316 that is disposed with the blind bore 302 of the body 294 and a second portion 318 that extends outside the body 294. The first portion 316 of cap 296 that is disposed within blind bore 302 can be generally cylindrical in shape. The second portion 318 of the cap 296 that extends outside the body 294 can be partially spherical or hemispherical in shape in accordance with an embodiment of the disclosure. The second portion 318 of the cap 296 that extends outside the body 294 includes at least one distal irrigation port 320 that is configured to direct irrigation fluid distally from the axially extending passageway 308. The distal irrigation port 320 can extend substantially radially relative to the body 294. The second portion 318 of the cap 296 can include a plurality of distal irrigation ports 320 in an embodiment of the disclosure. The cap 296 can include at least one port 322 for receiving a temperature sensing mechanism 324.

Although three embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

What is claimed is:

1. An irrigated ablation electrode assembly of an irrigation catheter, the assembly comprising:
a body having a proximal end coupled to a shaft of the irrigation catheter, the body including a longitudinal axis, a distal portion, and a proximal portion, the distal portion defining:
i) at least one irrigation port, and
ii) at least one axially extending passageway positioned off-axis from the longitudinal axis of the body, the at least one axially extending passageway configured to direct irrigation fluid from the proximal portion of the body to the distal portion of the body,
wherein the at least one irrigation port is configured to direct the irrigation fluid proximally from the at least one axially extending passageway.

2. The assembly of claim 1, wherein the at least one axially extending passageway extends for substantially a length of the distal portion of the body.

3. The assembly of claim 1, wherein the distal portion of the body comprises a distal portion outer diameter; the proximal portion of the body comprises a proximal portion outer diameter; and the distal portion outer diameter is larger than the proximal portion outer diameter.

4. The assembly of claim 1, further comprising:
a cap including a first portion that is disposed within a bore in the distal portion of the body and a second portion that extends outside the body, wherein the second portion of the cap includes at least one radially extending port.

5. The assembly of claim 4, wherein the first portion of the cap is generally cylindrical in shape and the second portion of the cap is partially hemispherical in shape.

6. The assembly of claim 1, wherein the body is comprised of an electrically conductive material.

7. The assembly of claim 1, wherein the body further comprises a proximal fluid compartment and a distal fluid compartment, and wherein the proximal and distal fluid compartments are connected by the at least one axially extending passageway.

8. The assembly of claim 7, further comprising:
an insert positioned between the proximal fluid compartment and the distal fluid compartment.

9. The assembly of claim 8, wherein the insert comprises a cap, the cap including a first portion that is disposed within a bore in the distal portion of the body and a second portion that extends outside the body.

10. The assembly of claim 7, wherein the irrigation port is positioned distally of the proximal fluid compartment and in fluid communication with the distal fluid compartment.

11. The assembly of claim 1, wherein the at least one irrigation port extends substantially axially relative to the body.

12. An irrigated ablation electrode assembly of an irrigation catheter, the assembly comprising:
a body having a proximal end coupled to a shaft of the irrigation catheter, the body including a longitudinal axis, a distal portion, and a proximal portion, wherein the distal portion defines an axially extending passageway positioned off-axis from the longitudinal axis of the body, wherein the axially extending passageway is configured to direct irrigation fluid from the proximal portion of the body to the distal portion of the body, an irrigation port in fluid communication with the axially extending passageway, the irrigation port configured to direct fluid proximally from the axially extending passageway.

13. The assembly of claim 12, further comprising:
a cap at least partially disposed within a bore in the distal portion of the body and including at least one cap port in fluid communication with the axially extending passageway.

14. The assembly of claim 13, wherein a first portion of the cap is generally cylindrical in shape and a second portion of the cap is partially hemispherical in shape.

15. The assembly of claim 13, wherein the at least one cap port extends radially and is configured to direct fluid distally.

16. An irrigated catheter assembly comprising:
a catheter shaft; and
an ablation electrode assembly having a proximal end coupled to the catheter shaft and disposed at a distal end of the catheter shaft, the ablation electrode assembly comprising:
a body including a longitudinal axis, a distal portion, and a proximal portion,
wherein the distal portion defines an irrigation port, and
wherein the distal portion of the body further defines at least one axially extending passageway positioned off-axis from the longitudinal axis of the body, the at least one axially extending passageway configured to direct irrigation fluid from the proximal portion of the body to the distal portion of the body, and the irrigation port is configured to direct a fluid proximally from the at least one axially extending passageway.

17. The assembly of claim 16, wherein the proximal portion of the body of the ablation electrode assembly is configured to couple the distal portion of the body to the catheter shaft.

18. The assembly of claim 17, wherein the proximal portion of the body of the ablation electrode assembly includes a plurality of radially outwardly extending threads.

19. The assembly of claim 16, wherein the body of the ablation electrode assembly includes at least one retaining port for receiving a retaining wire configured to couple the ablation electrode assembly with the catheter shaft.

20. The assembly of claim 19, wherein a portion of the retaining port extends into the body.

\* \* \* \* \*